United States Patent [19]

Grief et al.

[11] Patent Number: 5,360,454
[45] Date of Patent: Nov. 1, 1994

[54] TANNING OF LEATHER AND FUR

[75] Inventors: Norbert Grief, Bobenheim; Knut Oppenlaender; Hermann Birkhofer, both of Ludwigshafen; Brigitte Wegner, Roemerberg; Johannes P. Dix, Weisenheim, all of Germany

[73] Assignee: Basf Aktiengesellschaft, Ludwigshafen, Germany

[21] Appl. No.: 66,233

[22] Filed: May 25, 1993

[30] Foreign Application Priority Data

Jun. 13, 1992 [DE] Germany .............................. 4219419

[51] Int. Cl.$^5$ ..................... C14C 3/08; C07D 309/06
[52] U.S. Cl. ...................................... 8/94.33; 8/94.21; 252/8.57; 549/415
[58] Field of Search .................. 8/94.33, 94.21; 549/415; 252/8.57

[56] References Cited

U.S. PATENT DOCUMENTS 2,619,491 11/1952 Smith .................... 8/94.33

FOREIGN PATENT DOCUMENTS 2237963 2/1975 France .
1769059 8/1971 Germany .

Primary Examiner—Prince Willis, Jr.
Assistant Examiner—Alan D. Diamond
Attorney, Agent, or Firm—Oblon, Spivak, McClelland, Maier & Neustadt

[57] ABSTRACT

Abstract of the Disclosure: A process for tanning leather comprises using for this purpose compounds of the general formula I

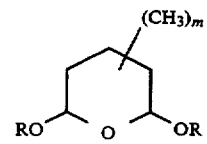

where
m is 0 or 1, and the radicals
R are independently of each other $C_1$-$C_{18}$-alkyl, which may be substituted by hydroxyl or carboxyl and/or interrupted by oxygen atoms, or else one of the radicals R is a radical of the formula

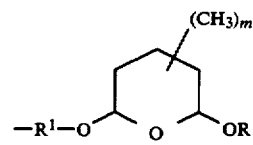

where
$R^1$ is alkylene, which may be substituted by hydroxyl and/or interrupted by oxygen atoms.

16 Claims, No Drawings

TANNING OF LEATHER AND FUR

The present invention relates to an improved process for self-tanning, pretanning and assist-tanning. of hide and skin pelts and for retanning leather and skin.

Aldehydes and in particular dialdehydes such as glutardialdehyde are frequently described in the literature, and used in practice, as tanning agents for leather. For instance, DE-A-1 769 059 concerns a process for making leather by treating tannable material with zinc salts, water-soluble sulfates and aldehydes or aldehyde donors and aftertreating with basifiers.

These processes and the leather and skin obtained by these processes frequently have a number of disadvantages. Glutardialdehyde in particular can give nonuniform results because of its high reactivity; this is especially the case with unsplit pelts, where low dialdehyde concentrations do not achieve complete penetration. Furthermore, because the aldehydes used are highly volatile and frequently very toxic or otherwise potentially injurious to health, safety measures need to be taken and, what is more, a relatively large amount of the aldehyde tanning agent needs to be used.

It is an object of the present invention to provide novel tanning agents for self-, pre-, assist- and re-tanning which are free of the disadvantages of the prior art.

We have found that this object is achieved by a process for tanning leather, which comprises using for this purpose compounds of the general formula I

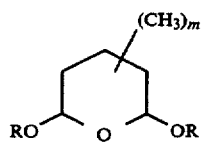

where
  m is 0 or 1, and the radicals
  R are independently of each other $C_1-C_{18}$-alkyl, which may be substituted by hydroxyl or carboxyl and/or interrupted by oxygen atoms, or else one of the radicals R is a radical of the formula

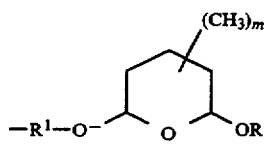

where
  $R^1$ is alkylene, which may be substituted by hydroxyl and/or interrupted by oxygen atoms.

$C_1-C_{18}$-Alkyl R can be linear or branched and is less preferably $C_9-C_{18}$, e.g. nonyl, decyl, dodecyl, tridecyl, tetradecyl, hexadecyl or octadecyl.

Hydroxycarboxylic acid radicals R are derived for example from the following acids: hydroxyacetic acid, hydroxypropionic acid, lactic acid or hydroxystearic acid.

These radicals R can of course also be present in the salt form, for example as lithium, sodium, potassium or substituted or unsubstituted ammonium salts.

R is in particular $C_1-C_8$-alkyl or $C_3-C_{40}$-oxaalkyl such as $CH_3$, $C_2H_5$, $C_3H_7$, $C_4H_9$, $C_5H_{11}$, $C_6H_{13}$, $C_7H_{15}$, $C_8H_{17}$,

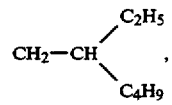

$CH_2CHOH-CH_2$, $(CH_2CH_2O)_2-CH_3$, $(CH_2CH_2O)_3CH_3$, $(CH_2CH_2O)_4CH_3$ or polyalkylene oxide groups.

A preferred group of radicals R conform to the formula

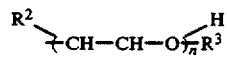

where
  n is from 1 to 20,
  $R^2$ is hydrogen or $C_1-C_4$-alkyl, and
  $R^3$ is hydrogen or $C_1-C_8$-alkyl.

$R^1$ is in particular of the formula

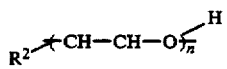

where $R^2$ and n are each as defined above.

From the preparation of the compounds of the formula I one of the radicals R is preferably $C_1-C_4$-alkyl, in particular methyl.

Preferred compounds conform to the formula Ia

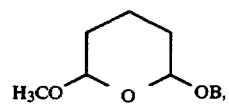

where
  B is a radical of the formula

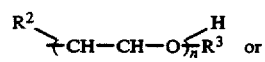

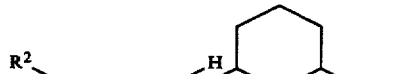

and n, $R^2$ and $R^3$ are each as defined above.

$R^2$ is preferably hydrogen and n is preferably from 4 to 10.

According to the invention it is important that the compounds of the formula I should be as water-soluble as possible. By varying and combining the various substituents it is a simple matter for a person skilled in the art to achieve this water solubility.

Of the compounds to be used according to the invention, those of the formula

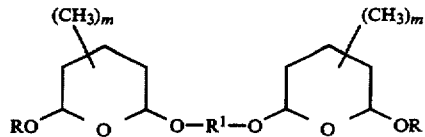

are novel; as regards the preferred meanings of the symbols, the above remarks apply.

The compounds of the formula I can be prepared by adding alcoholic hydroxy compounds to 2-alkoxy-3,4-di-hydro-2-pyrans in a conventional manner; a preferred pyran compound is 2-methoxy-3,4-dihydro-2-pyran. Details of the preparation can be found in the relevant Examples.

The tanning process of the present invention is highly suitable for self-tanning and pretanning hide and skin pelts in aqueous liquor. This is advantageously done by treating the pickled hide pelts, for example cattlehide pelts having a split thickness of from 1.5 to 4 mm, or skin pelts, for example sheepskin pelts, with an aqueous solution or dispersion of compounds I at a pH of from 2 to 7, in particular from 2.5 to 4, and at from 15° to 50° C., in particular at from 25° to 45° C., for a period of from 3 to 20 hours. The treatment takes for example the form of milling in a drum. The amount of compound I required is normally, based on the pelt weight, from 2 to 30% by weight, in particular from 5 to 20% by weight. The liquor length, i.e. the percentage weight ratio of treatment liquor to goods, is customarily from 30 to 200% in the case of hide pelts or from 100 to 2000% in the case of skin pelts, in either case based on the pelt weight.

On completion of the treatment the leather or skin is customarily brought to a pH of from 4 to 8, in particular 5 to 7, using for example magnesium oxide, sodium carbonate or sodium bicarbonate, optionally treated with further tanning agents and, on completion of the tanning process, optionally dyed and fatliquored.

The tanning process of the present invention is likewise highly suitable for assist-tanning hide and skin pelts together with the tanning agents of the main tannage, which can be for example a chrome or aluminum tannage. In this case the working conditions concerning pH, temperature and duration of treatment are adjusted to the requirements of the main components of the tannage; the same applies to the treatment apparatus and the liquor length and also to the aftertreatment. Here the amount of compound I required is normally, based on the pelt weight, from 0.1 to 20% by weight, in particular from 0.5 to 15% by weight.

The tanning process of the present invention is similarly highly suitable for retanning previously tanned leather and skin, for example chrome tanned leather, in an aqueous liquor. It is generally carried out by tanning the pickled pelts and skins, for example cattlehide pelts having split thicknesses of from 1.5 to 4 mm, with for example a customary chromium-containing tanning agent such as a chromium(III) salt, e.g. chromium(III) sulfate, in a conventional manner, deacidifying the resulting pretanned hides (wet blues in the case of chrome tanning) and treating the deacidified hides at a pH of from 2 to 7, in particular from 2.5 to 4, and at from 15° to 50° C., in particular at from 25° to 45° C., with an aqueous solution or dispersion of compounds I for a period of from 1 to 12 hours. This treatment takes for example the form of milling in a drum. The amount of compounds of the formula I required is normally, based on the shaved weight of the leather, from 2 to 30% by weight, in particular from 5 to 20% by weight. The liquor length is customarily from 30 to 200% in the case of hide pelts or from 100 to 2000% in the case of skin pelts, in either case based on the shaved weight of the leather.

After the treatment and if necessary also beforehand, the leather or skin is customarily adjusted to a pH of from 3 to 5, using for example magnesium oxide or an organic acid such as formic acid or salts thereof, and after the treatment it is dyed and fatliquored, if desired.

The leather or skin which has been retanned according to the present invention may have been additionally treated with other tanning agents such as Polymer tanning agents or suntans prior to the retanning with the compounds I. Moreover, the compounds I can be used simultaneously with such additional tanning agents, for example in the main tannage.

Suitable additional or simultaneous tanning agents are all customary agents having a tanning effect on hide or skin pelts. A comprehensive treatment of such tanning agents may be found for example in Ullmanns Encyklopädie der technischen Chemie, 3rd edition, volume 11, pages 585 to 612 (1960). Specific tanning agent classes which may be mentioned are the mineral tanning agents, for example chromium, aluminum, zinc or zirconium salts, the synthetic tanning agents such as the abovementioned polymer tanning agents and syntans, and the vegetable (plant-derived) tanning agents or tannins.

The tanning process of the present invention produces leathers and furs which, compared with the products obtained using the prior art aldehyde tanning agents such as glutardialdehyde, possess not only a full and very soft handle and high shrinkage temperatures but also a distinctly improved tensile and tear strength. Moreover, leathers and skins tanned according to the present invention are noticeably free of any yellow color. A clear advantage is the penetrating power of even small amounts of the compounds to be used according to the invention.

A further advantage of the tanning process of the present invention is the low volatility of the compounds of the formula I, as is evident for example from the comparatively small amount required of these tanning agents. Furthermore, the compounds I are in a certain sense universal tanning agents, since they can be combined with all other customary tanning agents and are usable not only for self-tanning, pretanning and assist-tanning but also for retanning.

General method for preparing compounds of the formula I

The addition of OH-containing products to 2-methoxy-3,4-dihydro-2-pyran is effected at from 50° to 100° C. by acid catalysis. Suitable acids are mineral, sulfonic and carboxylic acids. The reaction can be monitored by IR spectroscopy, since the C=C double bond band at 1650 cm$^1$ disappears in the course of the addition.

EXAMPLE 1

To 288 g of an addition product of ethylene oxide with glycol, molecular weight ~300, and 0.5 g of p-toluenesulfonic acid are added dropwise at 70° C. 219 g of 2-methoxy-3,4-dihydro-2-pyran (MOP), and in the course of the dropwise addition the temperature rises to 85° C. The reaction mixture is subsequently stirred at 85° C. for 30 min. Traces of unconverted MOP are then removed under reduced pressure.

Yield: 497.5 g

IR at 1650 cm$^{-1}$: low absorption.

EXAMPLE 2

Example 1 is repeated with 92.1 g of glycerol,
1 g of p-toluenesulfonic acid, and
114 g of MOP.
Yield: 205.5 g IR (1650 cm$^{-1}$)=low.

EXAMPLE 3

Example 1 is repeated with
97.3 g of glycolic acid and
146 g of MOP.
Yield: 242.3 g IR (1650 cm$^{-1}$)=low absorption.

USE EXAMPLES

EXAMPLE 4

Self-tanning of cattlehide pelts

Thoroughly delimed and pickled cattlehide pelt having a split thickness of 2 mm was admixed at a liquor length of 100% with 10% by weight, based on the pickled weight, of the compound prepared in Example 3, added in three portions, and drummed at room temperature and about pH 3 for 3 hours. Then the float was heated to 40° C. and adjusted to about pH 7 with magnesium oxide. After a brief rinse, the leather was finished as usual.

The result obtained was a white leather having a shrinkage temperature of about 85° C., which was very soft and pliable.

EXAMPLE 5

Example 4 was repeated with 8% by weight of the tanning agent prepared as described in Example 1. The leather obtained had a shrinkage temperature of about 83° C.

EXAMPLE 6

Use of compounds of the formula I in pretanning:

Thoroughly delimed and pickled cattlehide pelt having a split thickness of 2 mm was admixed at a liquor length of 50% with initially 1% of a fatliquor for 10 min and then, following addition of about 0.7% of the tanning agent prepared in Example 1 and 1% of a polymer tanning agent, drummed for a further 60 min. Thereafter 1% of a synthetic tanning agent was added and drumming was continued for a further 60 min. The pH was then adjusted overnight to 3.9 with magnesium oxide.

The result obtained was a very light-colored, pretanned leather which had a shrinkage temperature of about 70° C. and was satisfactorily shavable. By completing the tanning with chromium or aluminum salts, syntans or else vegetable tannins, this intermediate product can be converted into any type of leather.

EXAMPLE 7

Retanning of chrome-tanned cattlehide leather

A conventionally produced wet blue shaved to 1.5 mm was admixed in a 100% float with 2.5% by weight of tanning agent (synthesized as described in Example 1), based on the shaved weight, and drummed at 40° C. and about pH 3.4 for 90 min. The pH was then adjusted to about 4.6 with 1% by weight of sodium format and 0.5% by weight of sodium bicarbonate.

The subsequent dyeing and fatliquoring with commercial products and a customary finishing process produced a soft, full leather having a pleasant hand.

EXAMPLE 8

Retanning for soft box leather

Wet blue shaved to a thickness of 1.5 mm was initially washed and then drummed in a 50% by weight float (percentages are based on the shaved weight) with 2% by weight of a commercial, lightly blocked chrome tanning agent and 2.5% by weight of the tanning agent prepared as described in Example 1 for 45 min.

The pH was then adjusted to about 4 with 1% by weight of sodium formate. Following renewed washing the retanned leather was dyed with a customary leather dye, conventionally fatliquored and conventionally finished.

The result obtained was a very soft, full and pliable leather with a very level coloration.

We claim:

1. A process for tanning leather comprising contacting said leather with a compound of the formula I:

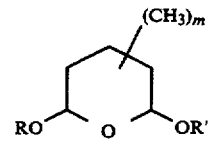

where m is 0 or 1,

R is an unsubstituted or substituted $C_{1-18}$ alkyl group wherein the substituents are hydroxyl; and R' is a radical of the formula -(CHR$^2$CH$_2$O)$_n$R$^3$ or -(CH$_2$CHR$^2$O)$_n$R$^3$ where n is 1 to 20 R$^2$ is hydrogen or a $C_{1-4}$ alkyl and R$^3$ is hydrogen or a $C_{1-8}$ alkyl or is a radical of the formula:

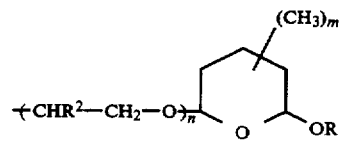

or

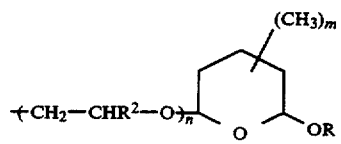

where m, n, R and R$^2$ are as defined above.

2. A process as claimed in claim 1, wherein said compounds have the formula

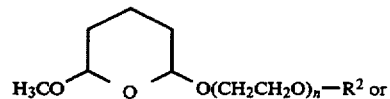

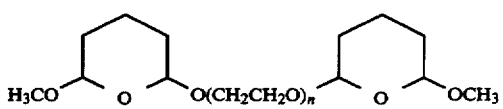

where n and R$^2$ are as defined in claim 1.

3. The process of claim 1, wherein R$^2$ is hydrogen.
4. The process of claim 1, wherein m is 0.
5. The process of claim 1, wherein n is 4 to 10.
6. The process of claim 1, wherein R$^2$ is hydrogen and n is 4 to 10.

7. The process of claim 1, wherein R is selected from the group consisting of $CH_3$, $C_2H_5$, $C_3H_7$, $C_4H_9$, $C_5H_{11}$, $C_6H_{13}$, $C_7H_{15}$, $C_8H_{17}$, $CH_3CHOH-CH_2$,

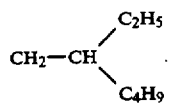

8. A process for tanning leather comprising contacting said leather with a compound of the formula I:

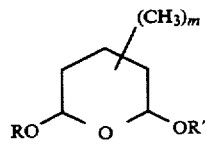

wherein m is 0 or 1,
R is methyl; and
R' is a radical of the formula $-(CHR^2CH_2O)_nR^3$ or $-(CH_2CHR^2O)_nR^3$ where n is from 1 to 20, $R^2$ is hydrogen or a $C_{1-4}$ alkyl and $R^3$ is hydrogen or a $C_{1-8}$ alkyl, or is a radical of the formula:

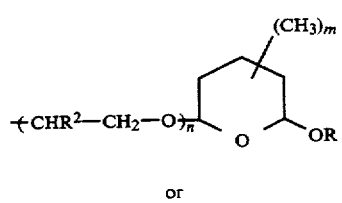

or

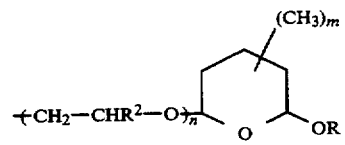

where m, n, R and $R^2$ are as defined above.

9. A compound of the formula:

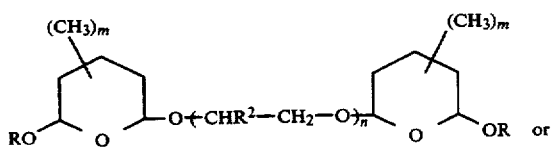

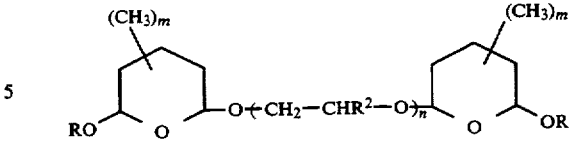

where m is 0 or 1,
R is an unsubstituted or substituted $C_{1-18}$ alkyl group wherein the substituents are hydroxyl; or a radical of the formula $-(CHR^2CH_2O)_nR^3$ or $-(CH_2CHR^2O)_nR^3$ wherein n is 1 to 20 $R^2$ is hydrogen or a $C_{1-4}$ alkyl, and $R^3$ is hydrogen or a $C_{1-8}$ alkyl.

10. Compounds of the formula as set forth in claim 9 where m is O and R is methyl.

11. The compound of claim 9, wherein $R^2$ is hydrogen.

12. The compound of claim 9, wherein m is O.

13. The compound of claim 9, wherein n is 4 to 10.

14. The compound of claim 9, wherein $R^2$ is hydrogen and n is from 4 to 10.

15. The compound of claim 9, wherein R is selected from the group consisting of $CH_3$, $C_2H_5$, $C_3H_7$, $C_4H_9$, $C_5H_{11}$, $C_6H_{13}$, $C_7H_{15}$, $C_8H_{17}$, $CH_2CH_2OCH_3$, $CH_2CH_2OC_2H_5$, $CH_2CH_2-OC_4H_9$, $CH_3CHOH-CH_2$, $(CH_2CH_2O)_2-CH_3$, $(CH_2CH_2O)_3CH_3$, $(CH_2CH_2O)_4CH_3$,

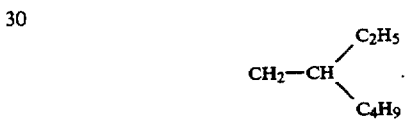

16. A compound of the formula:

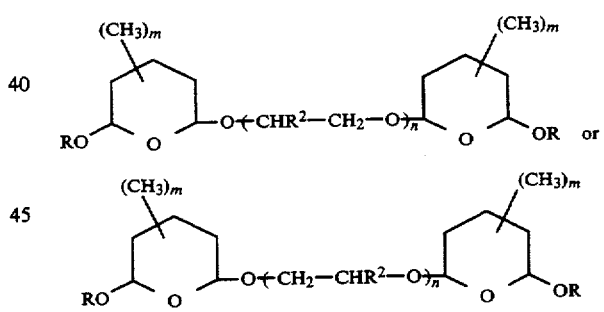

where m is 0 or 1, n is 1 to 20
R is methyl; and
$R^2$ is hydrogen or a $C_{1-4}$ alkyl.

* * * * *

UNITED STATES PATENT AND TRADEMARK OFFICE
CERTIFICATE OF CORRECTION

PATENT NO. : 5,360,454
DATED : November 1, 1994
INVENTOR(S) : Norbert GREIF, et al.

It is certified that error appears in the above-indentified patent and that said Letters Patent is hereby corrected as shown below:

On the title page, Items [19] and [75], the first inventor's last name is spelled incorrectly. It should read:

[19] --Greif et al.--

[75] --Norbert Greif--

Signed and Sealed this

Fourteenth Day of March, 1995

Attest:

BRUCE LEHMAN

*Attesting Officer*   *Commissioner of Patents and Trademarks*